United States Patent
Bennett et al.

(10) Patent No.: US 11,504,373 B2
(45) Date of Patent: Nov. 22, 2022

(54) COMPOUNDS AND COMPOSITIONS FOR TREATING FIBROSIS

(71) Applicant: YALE UNIVERSITY, New Haven, CT (US)

(72) Inventors: Anton Bennett, Wilton, CT (US);
Jonathan Ellman, Guilford, CT (US);
Haya Jamali, New Haven, CT (US);
Karen S. Anderson, Guilford, CT (US); Elias Lolis, Fairfield, CT (US);
Denton Hoyer, West Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/954,514

(22) PCT Filed: Dec. 18, 2018

(86) PCT No.: PCT/US2018/066191
§ 371 (c)(1),
(2) Date: Jun. 16, 2020

(87) PCT Pub. No.: WO2019/126141
PCT Pub. Date: Jun. 27, 2019

(65) Prior Publication Data
US 2020/0390770 A1 Dec. 17, 2020

Related U.S. Application Data

(60) Provisional application No. 62/607,110, filed on Dec. 18, 2017.

(51) Int. Cl.
*A61K 31/519* (2006.01)
*A61K 31/517* (2006.01)
*C07D 239/78* (2006.01)
*C07D 471/04* (2006.01)
*C07D 491/052* (2006.01)
*C07D 495/04* (2006.01)

(52) U.S. Cl.
CPC .......... *A61K 31/519* (2013.01); *A61K 31/517* (2013.01); *C07D 239/78* (2013.01); *C07D 471/04* (2013.01); *C07D 491/052* (2013.01); *C07D 495/04* (2013.01)

(58) Field of Classification Search
CPC .. A61K 31/517; A61K 31/519; C07D 487/04; C07D 239/70; C07D 491/052; C07D 495/04
See application file for complete search history.

(56) References Cited

U.S. PATENT DOCUMENTS

2010/0004256 A1  1/2010  Liu et al.

OTHER PUBLICATIONS

Shi et al., Improved regenerative myogenesis and muscular dystrophy in mice lacking Mkp5, The Journal of Clinical Investigation, vol. 123, No. 5, pp. 2064-2077 (2013).*
Extended European Search Report and Written Opinion dated Dec. 20, 2021 for European patent application No. 18890384.3.
"MAP Kinase Phosphatase-5 (MKP-5) as a novel anti-fibrotic therapeutic target", OCR7100: Non-Confidential, Jan. 4, 2017 (Jan. 4, 2017), pp. 1-20.
Tzouvelekis A. et al., "Loss of MAP Kinase Phosphatase 5 (MKP5) attenuates fibrotic responses in-vitro and in-vivo", International Journal of Medicine, vol. 109, No. Suppl. 1, 2016, p. 540.
Tzouvelekis A.E. et al., "Role of MAP Kinase Phosphatase 5 (MS) in Pulmonary Fibrosis", American Journal of Respiratory and Critical Care Medicine, vol. 193, 2016, p. A41.
Tuija Hommo et al., "Regulation of Inflammatory Cytokine Production by MKP-5 in Macrophages", Basic & Clinical Pharmacology & Toxicology, vol. 117, No. 2, Aug. 1, 2015 (Aug. 1, 2015), pp. 96-104.
PubChem CID 2820916, Jul. 19, 2005, Retrieved from the Internet <https://pubchem.ncbi.nlm.nih.gov/compound/2820916#section=2D-Structure>.
Wu et al. "Nepetoidin B, a Natural Product, Inhibits LPS-stimulated Nitric Oxide Production via 1, (4-5, 8)/1 Modulation of iNOS Mediated by NF-kB/MKP-5 Pathways" Phytother Res., Jul. 2017, vol. 31, No. 7, pp. 1072-1077.
Hommo et al. "Regulation of Inflammatory Cylokine Production by MKP-5 in Macrophages", Basic Clin Pharmacol Toxicol., Aug. 2015, vol. 117, No. 2, pp. 96-104.
International Search Report and Written Opinion issued for International Appl. No. PCT/US2018/066191 dated May 6, 2019.

* cited by examiner

*Primary Examiner* — Deepak R Rao

(74) *Attorney, Agent, or Firm* — Saul Ewing Arnstein & Lehr LLP; Kathryn Doyle; Domingos J. Silva

(57) ABSTRACT

The present invention provides compounds and methods for treating, ameliorating, and/or preventing a MKP-5 modulated disease. In certain embodiments, the MKP-5 modulated disease is a fibrotic disease.

12 Claims, 9 Drawing Sheets

Specification includes a Sequence Listing.

MKP5 Malachite Assay with pTpY Peptide

COMPOUNDS AND COMPOSITIONS FOR TREATING FIBROSIS

CROSS-REFERENCE TO RELATED APPLICATIONS

The present application is a 35 U.S.C. § 371 national phase application from, and claims priority to, International Application No. PCT/US2018/066191, filed Dec. 18, 2018, and published under PCT Article 21(2) in English, which claims priority under 35 U.S.C. § 119(e) to U.S. Provisional Patent Application No. 62/607,110, filed Dec. 18, 2017, all of which applications are incorporated herein by reference in their entireties.

STATEMENT REGARDING FEDERALLY SPONSORED RESEARCH OR DEVELOPMENT

This invention was made with government support under AR066003 awarded by National Institutes of Health. The government has certain rights in the invention.

BACKGROUND OF THE INVENTION

The accumulation of extracellular matrix components in response to tissue damage is a physiological process integral to tissue repair. Unfortunately, chronic insults that exacerbate injury precipitate overproduction of extracellular matrix components by fibroblasts and myofibroblasts, thus causing an excessive accumulation of fibrous connective tissue, which culminates in a pathological state known as fibrosis. Regardless of the etiology and intricate progressive complexities of many chronic diseases, fibrosis represents a common end-stage of tissue death. The destructive sequelae of tissue fibrosis results in organ dysfunction and eventually failure. As such, fibrosis is the single most common reason for organ transplantation.

Fibrosis can affect various organs such as the heart, liver, lung, skeletal muscle, kidney, vasculature and heart. Fibrosis represents the end-stage in a number of chronic tissue diseases representing nearly 50% of all deaths worldwide: skeletal muscle tissue (dystrophic muscle disease), cardiac and vascular tissue (myocardial infarction), liver tissue (non-alcoholic fatty liver disease/liver cirrhosis), lung tissue (idiopathic pulmonary fibrosis) and kidney tissue (chronic kidney disease/renal fibrosis).

For example, in dystrophic muscle disease (such as, for example, Duchenne muscular dystrophy), the dystrophic muscle becomes increasingly fibrotic, reducing the patient's ability to walk and jeopardizing the patient's breathing and cardiovascular function. There is no treatment or cure for dystrophic muscle diseases, and experimental gene replacement therapies have been unsuccessful.

In another example, idiopathic lung fibrosis (commonly referred to IDF or IPF) occurs in response to chronic lung injury, and is a chronic fibrotic parenchymal lung disease of unknown origin. Thickening and scaring of lung tissue reduces capacity of patients to breathe. IDF is common and more lethal than many cancers, with prevalence of 20-50 cases/100,000. The disease is generally diagnosed in subjects older than 55 years, and has a median survival time of 3-4 years. There are about 200,000 patients in the U.S. at any time, and 30,000 of those die every year.

Despite the increasing recognition that tissue fibrosis is the cause of significant morbidity and mortality of many diseases, there are few available FDA-approved treatments for fibrosis.

Mitogen-activated protein (MAP) kinases (also known as MAPKs) are protein kinases that are specific to the amino acids serine, threonine, and tyrosine. MAPKs are involved in directing cellular responses to a diverse array of stimuli, such as mitogens, osmotic stress, heat shock and proinflammatory cytokines. They regulate cell functions including proliferation, gene expression, differentiation, mitosis, cell survival and apoptosis.

On the other hand, MAP kinase phosphatases (MKPs) dephosphorylate the MAP kinases. Specifically, MKP-5 dephosphorylates p38 MAPK and JNK. The MAP kinases have been implicated in the progression of tissue fibrosis. Based on multiple mouse models in which injurious tissue repair proceeds to a fibrotic end-stage, MKP-5 has been shown to be a critical positive regulator of tissue fibrosis. Genetic inhibition of MKP-5 ameliorates fibrosis in the lung and skeletal muscle, and curtails the early events that occur in vascular fibrosis and atherogenesis. At the mechanistic level, MKP-5-deficient cells are impaired in their ability to activate the TGF-beta signaling pathway, which plays an established role in promoting fibrosis. These combined observations implicate MKP-5 as a target for tissue fibrosis therapy.

There is a need in the art for novel compounds and compositions that can be used to treat and/or prevent fibrotic disease. The present disclosure addresses this need.

BRIEF SUMMARY OF THE INVENTION

In one aspect, the invention provides a method of treating or preventing a MKP-5-modulated disease or disorder in a mammal in need thereof. In various embodiments, the method comprises administering to the mammal a therapeutically effective amount of a compound of formula (1a) or (1b):

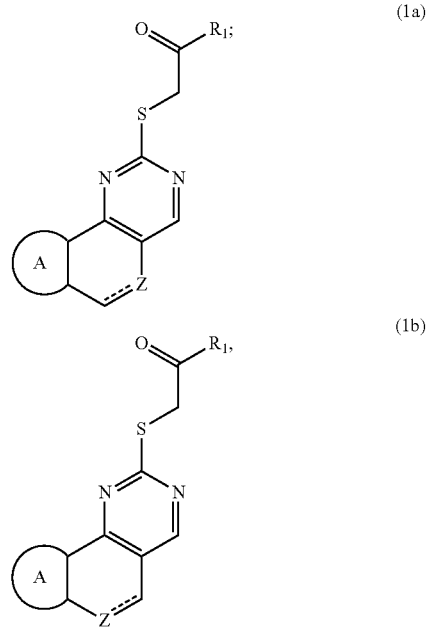

wherein: Z is selected from the group consisting of NR, NC(=O)R, CH$_2$ and O and the ====== bond is single; or Z is N and the ====== bond is double; R$_1$ is selected from the group consisting of C$_1$-C$_6$ alkyl, optionally substituted phenyl and NRR; each occurrence of R is independently selected from the group consisting of H, $C_1$-$C_6$ alkyl and optionally substituted phenyl; A is selected from the group consisting of optionally substituted phenyl and optionally substituted heteroaryl.

In various embodiments, the compound is the compound of formula (2):

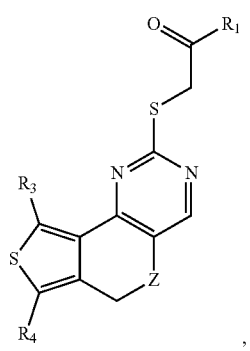

(2)

wherein: Z is selected from the group consisting of $CH_2$ and O; $R_1$ is selected from the group consisting of $C_1$-$C_6$ alkyl, optionally substituted phenyl and NRR, where each occurrence of R is independently selected from the group consisting of H, $C_1$-$C_3$ alkyl and substituted or unsubstituted phenyl; $R_3$ is selected from the group consisting of H, $C_1$-$C_6$ alkyl, and $C_1$-$C_3$ thioether; and $R_4$ is selected from the group consisting of H and $COOR_5$, where $R_5$ is selected from the group consisting of H and $C_1$-$C_6$ alkyl.

In various embodiments, the aryl or heteroaryl is substituted with at least one substituent selected from the group consisting of $C_1$-$C_6$ alkyl, $C_1$-$C_6$ thioalkyl, C(=O)OH, C(=O)OC_1$-$C_6$ alkyl, cyano and halo.

In various embodiments, the compound has a Ki≤100 μM against MKP-5.

In various embodiments, the compound binds to an allosteric site of MKP-5.

In various embodiments, the compound is selected from the group consisting of 3,3-dimethyl-1-((9-(methylthio)-5,6-dihydrothieno[3,4-h]quinazolin-2-yl)thio)butan-2-one; 1-((5,6-dihydrobenzo[h]quinazolin-2-yl)thio)-3,3-dimethylbutan-2-one; N,N-dimethyl-2-((9-(methylthio)-5,6-dihydrothieno[3,4-h]quinazolin-2-yl)thio)acetamide; N-ethyl-N-methyl-2-((9-(methylthio)-5,6-dihydrothieno[3,4-h]quinazolin-2-yl)thio)acetamide; 1-((9-fluoro-5,6-dihydrobenzo[h]quinazolin-2-yl)thio)-3,3-dimethylbutan-2-one; 1-((6H-isochromeno[4,3-d]pyrimidin-2-yl)thio)-3,3-dimethylbutan-2-one; 1-(2,4-dichlorophenyl)-2-((4-(3,4-dimethylthieno[2,3-b]thiophen-2-yl)pyrimidin-2-yl)thio) ethan-1-one; 1-((5,6-dihydrothieno[2,3-h]quinazolin-2-yl)thio)-3,3-dimethylbutan-2-one; 3,3-dimethyl-1-(pyrimido[5,4-c]quinolin-2-ylthio)butan-2-one; and 1-((6-acetyl-5,6-dihydropyrimido[5,4-c]quinolin-2-yl)thio)-3,3-dimethylbutan-2-one; and 3,3-dimethyl-1-((9-propyl-5,6-dihydrothieno[3,4-h]quinazolin-2-yl)thio)butan-2-one.

In various embodiments, the compound is selected from the group consisting of YU032149, HJ830, HJ845, HJ846, HJ858, and HJ862.

In various embodiments, the compound is administered as part of a pharmaceutical composition further comprising at least one pharmaceutically acceptable carrier.

In various embodiments, the MKP-5 modulated disease or disorder is a fibrotic disease or disorder.

In various embodiments, the MKP-5 modulated disease or disorder is selected from the group consisting of dystrophic muscle disease, a cardiac or vascular disease, idiopathic pulmonary fibrosis, and any combinations thereof.

In various embodiments, the mammal is a human.

In various embodiments, the MKP-5 inhibitor is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

In various embodiments, the method further comprises administering to the mammal at least one additional agent that treats or prevents the MKP-5 modulated disease or disorder in the mammal.

In various embodiments, the inhibitor and at least one additional agent are coformulated.

In another aspect, the invention provides a compound selected from the group consisting of.

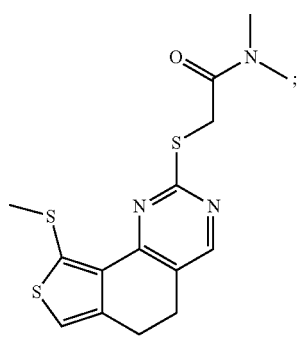

(4)

HJ845

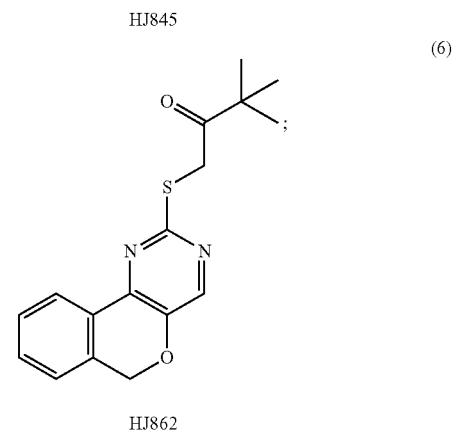

(6)

HJ862

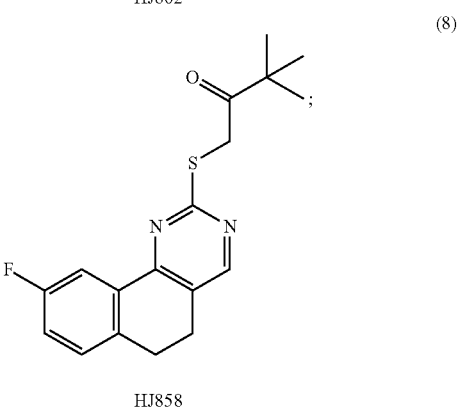

(8)

HJ858

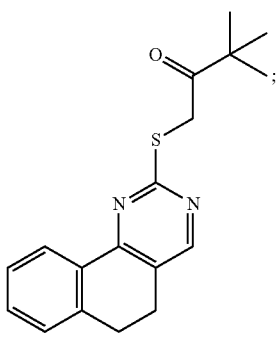

HJ830

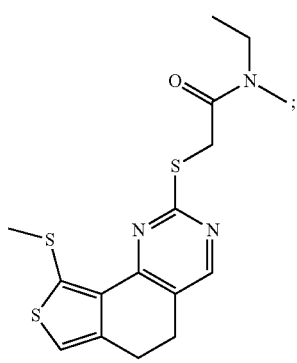

HJ846

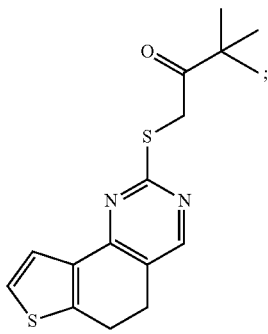

YU252252

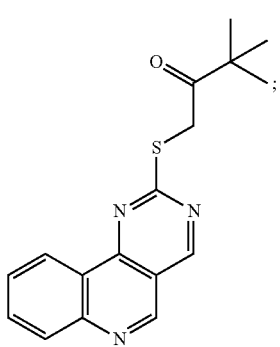

YU241658

(9)

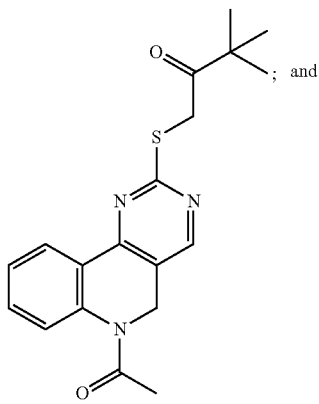

YU241659

(10)

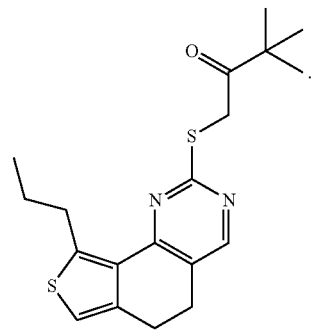 [SMILES: CCCc1scc2c1-c1nc(SCC(=O)C(C)(C)C)ncc1CC2]

In another aspect, the invention provides a kit for preventing or treating a MKP-5 modulated disease or disorder in a mammal, the kit comprising a MKP-5 inhibitor, optionally an applicator, and an instructional material for use thereof, wherein the instructional material recites the amount of, and frequency with which, the MKP-5 inhibitor is to be administered to the mammal to treat or prevent the MKP-5 modulated disease or disorder.

In yet another aspect, the invention provides a method of determining if a test compound is a MKP-5 inhibitor. In certain embodiments, the method comprises contacting a test compound with (i) a substrate peptide comprising the amino acid sequence pThr-Gly-pTyr and (ii) a catalytic polypeptide comprising and/or consisting of the catalytic domain of MKP-5, or an active fragment thereof, thus forming a composition. In other embodiments, the method comprises measuring MKP-5 activity in the composition. In yet other embodiments, the method comprises comparing the MKP-5 activity in the composition to a control. In yet other embodiments, the substrate peptide comprises the amino acid sequence Asp-Asp-Glu-Nle-pThr-Gly-pTyr-Val-Ala-Thr-Arg (pTpY, SEQ ID NO:3). In yet other embodiments, the measuring of MKP-5 activity comprises measuring any change in inorganic free phosphate in the composition.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

DETAILED DESCRIPTION OF THE INVENTION

Figure 1:
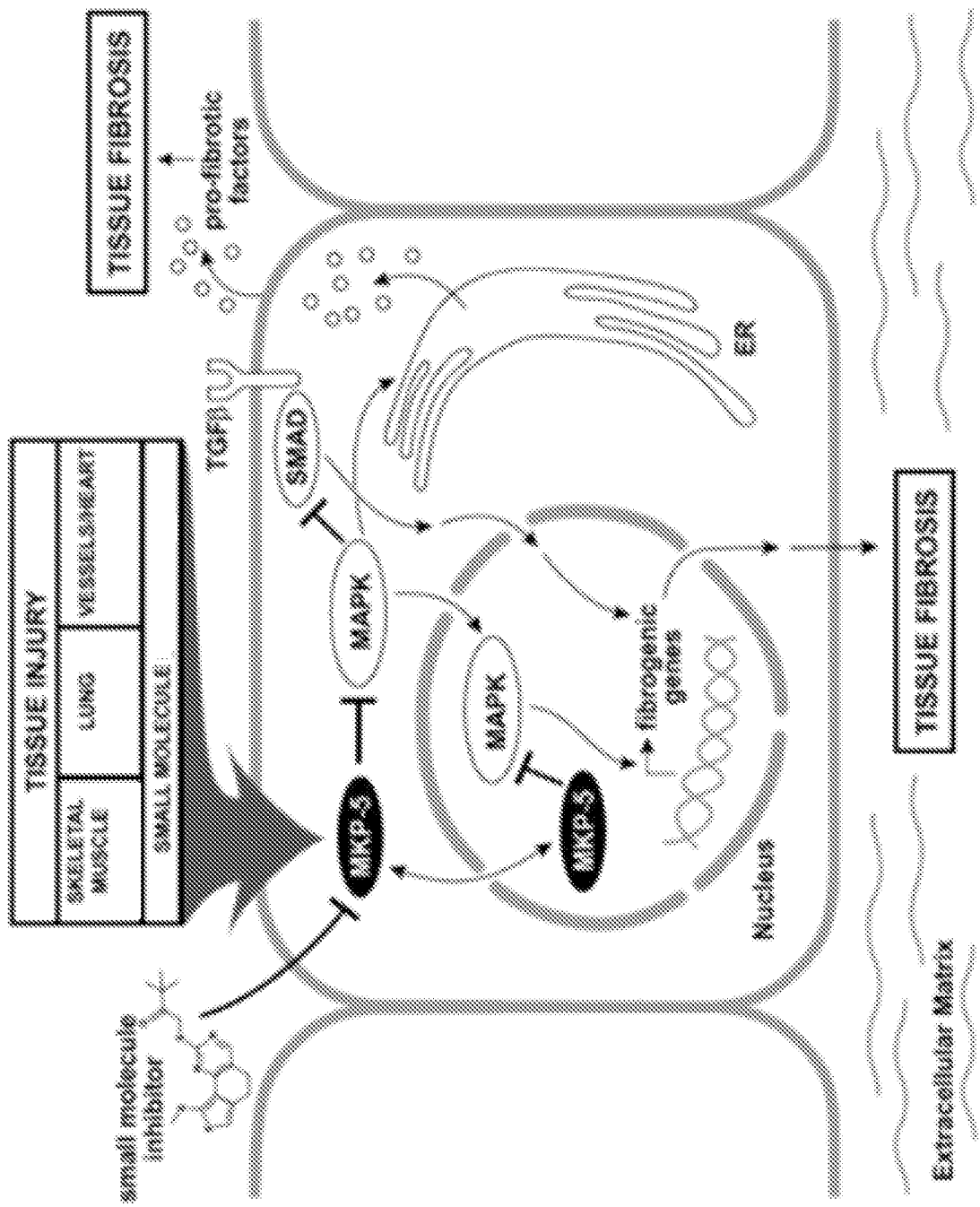
FIG. 1 comprises a schematic depicting illustrative roles of MKP-5 in tissue fibrosis.

The present invention relates in part to the identification of novel MKP-5 inhibitors, which find use in treating and/or preventing fibrosis. The present invention provides novel inhibitors of MKP-5, as well as compositions comprising the same, and their use in treating and/or preventing fibrosis. For example, compound YU032149 inhibits MKP-5 with an $IC_{50}$ of about 12 M. In certain embodiments, compounds of the invention inhibit MKP-5 through an allosteric mode of inhibition.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, each of the following terms has the meaning associated with it in this section.

Generally, the nomenclature used herein and the laboratory procedures in cell culture, molecular genetics, pharmacology and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or 10%, more preferably +5%, even more preferably +1%, and still more preferably 0.1% from the specified value, as such variations are appropriate to perform the disclosed methods.

A disease or disorder is "alleviated" if the severity or frequency of at least one sign or symptom of the disease or disorder experienced by a patient is reduced.

As used herein, the terms "analog," "analogue," or "derivative" are meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically.

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine. Additional examples include swaps within groups such as Gly/Ala; Val/Ile/Leu; Asp/Glu; Asn/Gln; Ser/Thr; Lys/Arg; and Phe/Tyr.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" or "therapeutically effective amount" of a compound is that amount of compound sufficient to provide a beneficial effect to the subject to which the compound is administered. An "effective amount" of a delivery vehicle is that amount sufficient to effectively bind or deliver a compound.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The term "MKP-5" or "MKP5" or "DUSP10" as used herein refers to the protein known as dual specificity protein phosphatase 10 or mitogen-activated protein kinase phosphatase 5 (see, for example, Tao & Tong, 2007, Protein Sci.

16(5):880-886, which is incorporated herein in its entirety by reference). This protein phosphatase is involved in the inactivation of MAP kinases, and has a specificity for the MAPK11-MAPK12-MAPK13-MAPK14 subfamily. In certain embodiments, MKP-5 dephosphorylates p38. Human MKP-5 corresponds to the polypeptide of amino acid sequence of SEQ ID NO:4. In certain embodiments, the MAP kinase binding domain of human MKP-5 corresponds to residues 139-287 of SEQ ID NO:4, and the catalytic domain of human MKP-5 corresponds to residues 305-482 of SEQ ID NO:4.

SEQ ID NO:4 is provided herein:

```
         10         20         30         40
MPPSPLDDRV VVALSRPVRP QDLNLCLDSS YLGSANPGSN 50         60         70         80
SHPPVIATTV VSLKAANLTY MPSSSGSARS LNCGCSSASC 90        100        110        120
CTVATYDKDN QAQTQAIAAG TTTTAIGTST TCPANQMVNN 130        140        150        160
NENTGSLSPS SGVGSPVSGT PKQLASIKII YPNDLAKKMT 170        180        190        200
KCSKSHLPSQ GPVIIDCRPF MEYNKSHIQG AVHINCADKI 210        220        230        240
SRRRLQQGKI TVLDLISCRE GKDSFKRIFS KEIIVYDENT 250        260        270        280
NEPSRVMPSQ PLHIVLESLK REGKEPLVLK GGLSSFKQNH 290        300        310        320
ENLCDNSLQL QECREVGGGA SAASSLLPQP IPTTPDIENA 330        340        350        360
ELTPILPFLF LGNEQDAQDL DTMQRLNIGY VINVTTHLPL 370        380        390        400
YHYEKGLFNY KRLPATDSNK QNLRQYFEEA FEFIEEAHQC 410        420        430        440
GKGLLIHCQA GVSRSATIVI AYLMKHTRMT MTDAYKFVKG 450        460        470        480
KRPIISPNLN FMGQLLEFEE DLNNGVTPRI LTPKLMGVET

VV
```

The phrase "MKP-5 inhibitor" or "inhibitor of MKP-5" as used herein refers to a composition or compound that inhibits at least in part, as compared to the control system that lacks the inhibitor, MKP-5 activity, MKP-5 expression and/or both, either directly or indirectly, using any method known to the skilled artisan. A MKP-5 inhibitor can be any type of compound, including but not limited to, a nucleic acid, peptide, antibody, small molecule, antagonist, aptamer, or peptidomimetic.

As used herein, an "MKP-5 modulated disease" or "MKP-5 modulated disorder" refers to a disease associated with pathological accumulation of excessive extracellular matrix proteins in an organ or tissue. Non-limiting examples of such diseases encompass, but are not limited to, cystic fibrosis or idiopathic pulmonary fibrosis.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" or "therapeutically acceptable salt" refers to a salt of the administered compounds prepared from pharmaceutically acceptable non-toxic acids, including inorganic acids or bases, organic acids or bases, solvates, hydrates, or clathrates thereof.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein, the terms "polypeptide," "protein" and "peptide" are used interchangeably and refer to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

By the term "specifically binds," as used herein, is meant a molecule, such as an antibody, which recognizes and binds to another molecule or feature, but does not substantially recognize or bind other molecules or features in a sample.

A "therapeutic" treatment is a treatment administered to a subject who exhibits signs of pathology, for the purpose of diminishing or eliminating those signs.

As used herein, the term "therapeutically effective amount" is an amount of a compound of the invention, that when administered to a patient, ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, "treating a disease or disorder" means reducing the frequency with which a symptom of the disease or disorder is experienced by a patient. Disease and disorder are used interchangeably herein.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

As used herein, the term "wild-type" refers to the genotype and phenotype that is characteristic of most of the members of a species occurring naturally and contrasting with the genotype and phenotype of a mutant.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Certain specific examples include ($C_1$-$C_6$)alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Certain specific examples include ($C_3$-$C_6$)cycloalkyl, such as, but not limited to, cyclopropyl, cyclobutyl, cyclopentyl and cyclohexyl.

As used herein, the term "substituted alkyl" or "substituted cycloalkyl" means alkyl or cycloalkyl, as defined above, substituted by one, two or three substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(═O) OH, trifluoromethyl, —C≡N, —C(═O)O($C_1$-$C_4$)alkyl, —C(═O)$NH_2$, —C(═O)NH($C_1$-$C_4$)alkyl, —C(═O)N(($C_1$-$C_4$)alkyl)$_2$, —$SO_2NH_2$, —C(═NH)$NH_2$, and —$NO_2$, advantageously containing one or two substituents selected from halogen, —OH, alkoxy, —$NH_2$, trifluoromethyl, —$N(CH_3)_2$, and —C(═O)OH, more advantageously selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In certain embodiments, alkoxy includes ($C_1$-$C_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, advantageously, fluorine, chlorine, or bromine, more advantageously, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(═O)—$CH_3$. Up to two heteroatoms may be consecutive, such as, for example, —$CH_2$—NH—$OCH_3$, or —$CH_2$—$CH_2$—S—S—$CH_3$.

As used herein, the term "aromatic" refers to a carbocycle or heterocycle with one or more polyunsaturated rings and having aromatic character, i.e. having (4n+2) delocalized 7 (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In certain embodiments, aryl includes phenyl and naphthyl, in particular, phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet another embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, in particular, straight.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Methods

In certain embodiments, the invention comprises treating a MKP-5 modulated disease by administrating a MKP-5 inhibitor. In certain embodiments, the MKP-5 modulated disease is any disease that can be treated or prevented by inhibition of MKP-5. In other embodiments, the invention comprises a method of treating fibrotic disease by administering a MKP-5 inhibitor to a patient. In yet other embodiments, the MKP-5 modulated disease is dystrophic muscle disease, a cardiac or vascular disease, idiopathic pulmonary fibrosis, and any combinations thereof.

Compounds and Compositions

In one aspect, the invention provides a compound of formula (1a) or (1b):

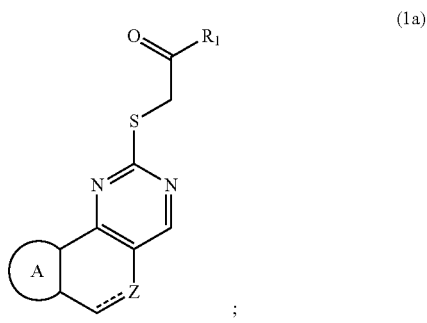

(1a)

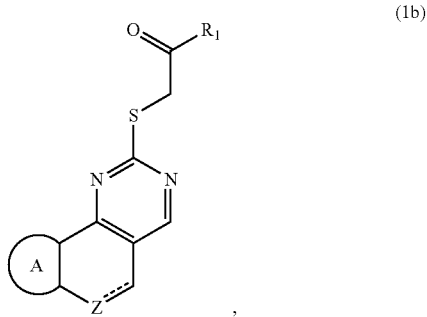

(1b)

wherein:

Z is selected from the group consisting of NR, NC(=O)R, $CH_2$ and O and the ====== bond is single; or Z is N and the ====== bond is double;

$R_1$ is selected from the group consisting of $C_1$-$C_6$ alkyl, optionally substituted phenyl and NRR;

each occurrence of R is independently selected from the group consisting of H, $C_1$-$C_6$ alkyl and optionally substituted phenyl;

A is selected from the group consisting of optionally substituted phenyl and optionally substituted heteroaryl.

In certain embodiments, the aryl or heteroaryl is substituted with at least one substituent selected from the group consisting of $C_1$-$C_6$ alkyl, $C_1$-$C_6$ thioalkyl, C(=O)OH, C(=O)O$C_1$-$C_6$ alkyl, cyano and halo.

In another aspect, the invention provides a compound of formula (2):

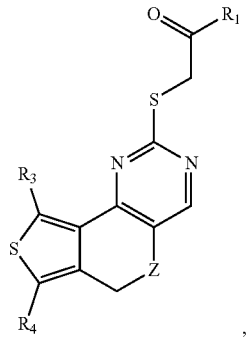

(2)

wherein:

Z is selected from the group consisting of CH$_2$ and O;

R$_1$ is selected from the group consisting of C$_1$-C$_6$ alkyl, optionally substituted phenyl and NRR;

each occurrence of R is independently selected from the group consisting of H, C$_1$-C$_3$ alkyl and substituted or unsubstituted phenyl;

R$_3$ is selected from the group consisting of H, C$_1$-C$_6$ alkyl, and C$_1$-C$_3$ thioether; and R$_4$ is selected from the group consisting of H and COOR$_5$, where R$_5$ is selected from the group consisting of H and C$_1$-C$_6$ alkyl.

In certain embodiments, the compound is selected from the group consisting of:

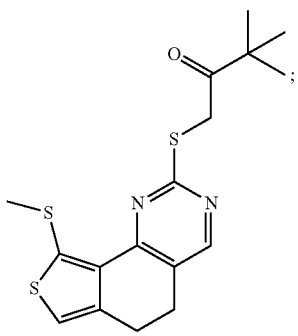

(3)

YU032149

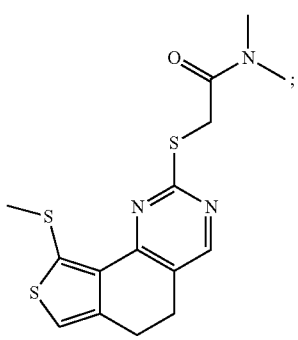

(4)

HJ845

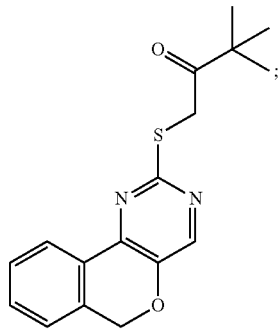

(6)

HJ862

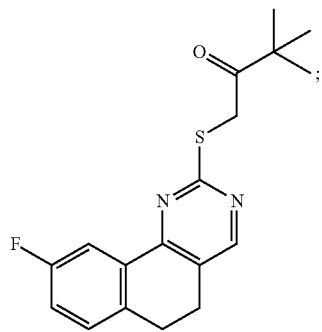

(8)

HJ858

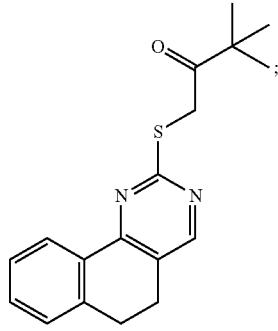

(9)

HJ830

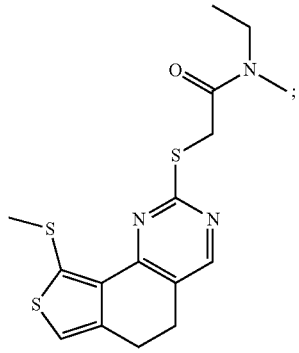

(10)

HJ846

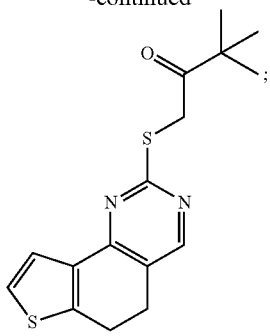

YU252252

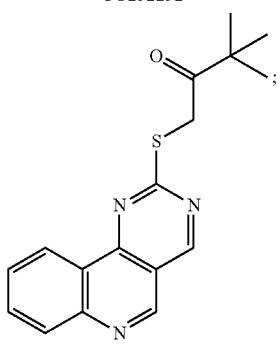

YU241658

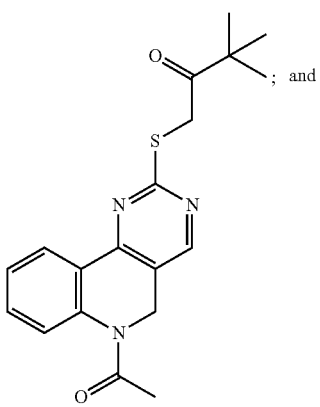

; and

YU241659

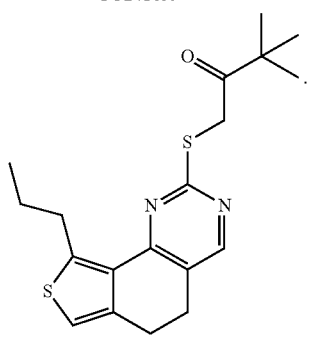

In certain embodiments, the compound is selected from the group consisting of: 3,3-dimethyl-1-((9-(methylthio)-5,6-dihydrothieno[3,4-h]quinazolin-2-yl)thio)butan-2-one; 1-((5,6-dihydrobenzo[h]quinazolin-2-yl)thio)-3,3-dimethylbutan-2-one; N,N-dimethyl-2-((9-(methylthio)-5,6-dihydrothieno[3,4-h]quinazolin-2-yl)thio)acetamide; N-ethyl-N-methyl-2-((9-(methylthio)-5,6-dihydrothieno[3,4-h]quinazolin-2-yl)thio)acetamide; 1-((9-fluoro-5,6-dihydrobenzo[h]quinazolin-2-yl)thio)-3,3-dimethylbutan-2-one; 1-((6H-isochromeno[4,3-d]pyrimidin-2-yl)thio)-3,3-dimethylbutan-2-one; 1-(2,4-dichlorophenyl)-2-((4-(3,4-dimethylthieno[2,3-b]thiophen-2-yl)pyrimidin-2-yl)thio)ethan-1-one; 1-((5,6-dihydrothieno[2,3-h]quinazolin-2-yl)thio)-3,3-dimethylbutan-2-one; 3,3-dimethyl-1-(pyrimido[5,4-c]quinolin-2-ylthio)butan-2-one; and 1-((6-acetyl-5,6-dihydropyrimido[5,4-c]quinolin-2-yl)thio)-3,3-dimethylbutan-2-one; and 3,3-dimethyl-1-((9-propyl-5,6-dihydrothieno[3,4-h]quinazolin-2-yl)thio)butan-2-one.

In certain embodiments, the compound is

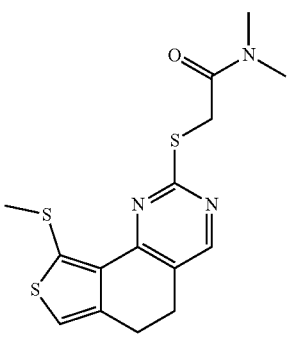

HJ845 (4)

In certain embodiments, the compound is

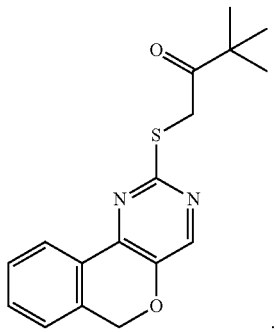

HJ862 (6)

In certain embodiments, the compound is

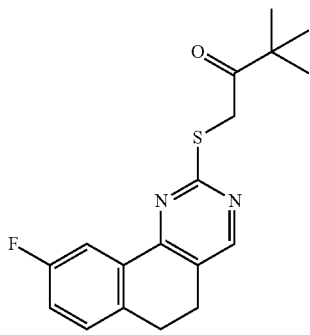

HJ858 (8)

In certain embodiments, the compound is

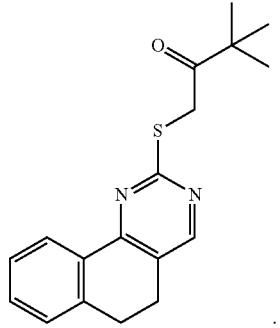

In certain embodiments, the compound is

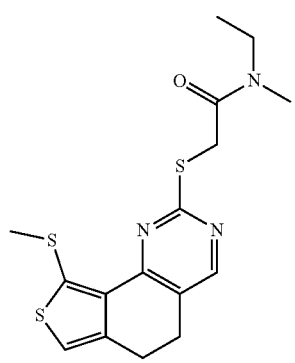

In certain embodiments, the compound is

YU252252

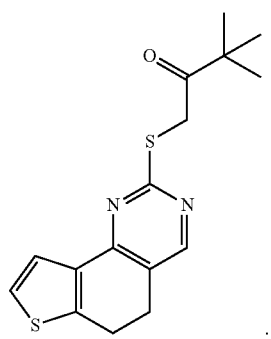

In certain embodiments, the compound is

HJ830 (9)

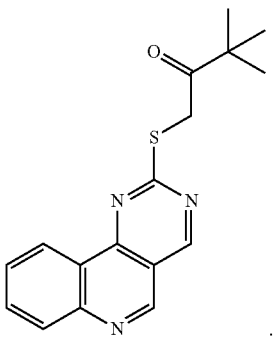

In certain embodiments, the compound is

HJ846 (10)

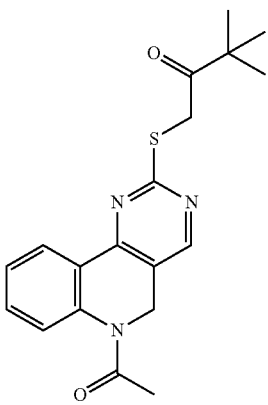

In certain embodiments, the compound is

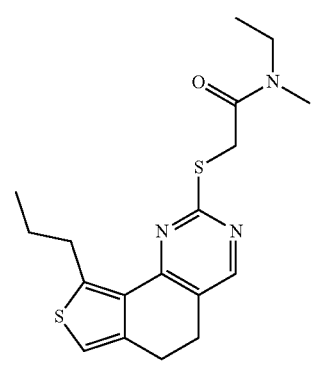

YU241658

YU241659

Combination Therapies

In certain embodiments, the compounds of the invention are useful in the methods of the invention in combination with at least one additional agent useful for treating or preventing an MKP-5 modulated disease in a mammal in need thereof. This additional agent can comprise compounds identified herein or compounds, e.g., commercially available compounds, known to treat, prevent or reduce the symptoms of the MKP-5 modulated disease in a subject.

In certain embodiments, the at least one additional compound useful for treating or preventing an MKP-5 modulated disease comprises acetylcholinesterase inhibitors, such as, but not limited to ninetedanib (Methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate) or pirfenidone (5-Methyl-1-phenylpyridin-2-one).

A synergistic effect may be calculated, for example, using suitable methods such as, for example, the Sigmoid-Emax equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Method of Screening Compounds as MKP-5 Inhibitors

In one aspect, the invention provides a method of identifying a compound that inhibits MKP-5. In certain embodiments, the method comprises contacting a putative inhibitor compound with (i) a substrate peptide comprising the sequence pThr-Gly-pTyr and (ii) a catalytic polypeptide comprising and/or consisting of the catalytic domain of MKP-5 (such as but not limited to residues 305-482 of SEQ ID NO:4), or an active fragment thereof, thus forming a composition. In other embodiments, the method comprises measuring MKP-5 activity in the composition. In yet other embodiments, the method comprises comparing the MKP-5 activity in the composition to a control; thereby identifying the putative inhibitor compound as a compound that inhibits MKP-5.

In certain embodiments, the catalytic polypeptide has at least about 60%, 65%, 70%, 75%, 80%, 85%, 86%, 87%, 88%, 89%, 90%, 91%, 92%, 93%, 94%, 95%, 96%, 97%, 98%, 99%, and/or 100% homology with human MKP-5 in the amino acid sequence corresponding to the catalytic domain of MKP-5. Conservative substitutions is contemplated within such homology.

In certain embodiments, the catalytic polypeptide has at least about 60%, 65%, 70%, 75%, 80%, 85%, 86%, 87%, 88%, 89%, 90%, 91%, 92%, 93%, 94%, 95%, 96%, 97%, 98%, 99%, and/or 100% sequence identity with human MKP-5 in the amino acid sequence corresponding to the catalytic domain of MKP-5.

In certain embodiments, the method is practiced as a high-throughput screen by which a plurality of compounds (putative inhibitors) are contacted with a peptide comprising pThr-Gly-pTyr and a polypeptide comprising and/or consisting of the catalytic domain of MKP-5 or an active fragment thereof, and inhibitors are identified from among the plurality of compounds by comparing their individual activities to a control.

Without wishing to be limited by theory, including a peptide encompassing the pThr180-Gly-pTyr182 motif of p38a MAPK (which is present on the activation loop of p38a MAPK and represents the primary MKP-5 substrate) in the assay uncovers more selective and thus more useful inhibitor compounds. In various embodiments, the peptide comprises SEQ ID NO: 3 (Asp-Asp-Glu-Nle-pThr-Gly-pTyr-Val-Ala-Thr-Arg), wherein Nle is norleucine.

A person of skill in the art will recognize that activity can be measured by combining the substrate and a polypeptide comprising and/or consisting of MKP-5 or any catalytically active fragment therefore, i.e. a polypeptide comprising and/or consisting of the MKP-5 catalytic domain or an active fragment thereof. A person of skill in the art will appreciate that a variety of methods of measuring MKP-5 activity and controls are possible and will be familiar with the same by analogy to activity assays. The control can be, by way of non-limiting example, a predetermined reference or may be a reaction performed without a MKP-5 inhibitor and/or without a peptide comprising pThr-Gly-pTyr.

In a non-limiting example, the assay comprises contacting a peptide comprising the sequence pThr-Gly-pTyr, the polypeptide comprising and/or consisting of the catalytic domain of MKP-5 (such as but not limited to residues 305-482 of SEQ ID NO:4), or an active fragment thereof, and the test compound. If the test compound is a MKP-5 inhibitor, it will inhibit the dephosphorylation of the peptide comprising the sequence pThr-Gly-pTyr. If the test compound is not a MKP-5 inhibitor, it will not inhibit the dephosphorylation of the peptide comprising the sequence pThr-Gly-pTyr. Dephosphorylation of that peptide can be evaluated qualitatively and/or quantitatively using any methods known in the art, such as but not limited to a Malachite Green Phosphate Assay. This assay provides a fast, reproducible, colorimetric method for measuring inorganic free phosphate in aqueous solutions. The assay method is based on the formation of a complex between malachite green molybdate and free orthophosphate that absorbs at 620-640 nm. This assay is a reliable and suitable means of detecting and quantifying minimal amounts of inorganic free phosphate and is amenable to high-throughput screening applications.

Kits

The invention includes a kit comprising at least one MKP-5 inhibitor, optionally an applicator, and instructional material for use thereof.

The instructional material included in the kit comprises instructions for preventing or treating a MKP-5-modulated disease in a mammal. The instructional material recites the amount of, and frequency with which, the MKP-5 inhibitor should be administered to the mammal. In certain embodiments, the kit further comprises at least one additional agent that prevents or treats an MKP-5-modulated disease in a mammal. In other embodiments, the kit further comprises at least one additional agent that improves and/or prevent further loss of cognition in a mammal.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from ng/kg/day and 100 mg/kg/day. In certain embodiments, the invention envisions administration of a dose which results in a concentration of the compound of the present invention from 1 M and 10 M in a mammal. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle.

The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-fibrotic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

In certain embodiments, the tablets of the invention comprise saracatinib difumarate, mannitol, dibasic calcium phosphate anhydrous, crospovidone, hypromellose and magnesium stearate, with a film-coat containing hypromellose, macrogol 400, red iron oxide, black iron oxide and titanium dioxide. In other embodiments, the tablets of the invention comprise about 50 or 125 mg of saracatinib expressed as free base. In yet other embodiments, the tablets of the invention comprise about 71.4 or 178.6 mg of saracatinib expressed as difumarate salt.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulfate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation". For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using anon-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. The data obtained from cell culture assays and animal studies are optionally used in formulating a range of dosage for use in human. The dosage of such compounds lies preferably within a range of circulating concentrations that include the ED50 with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Assay for MKP-5 Inhibitors

Figure 2A:
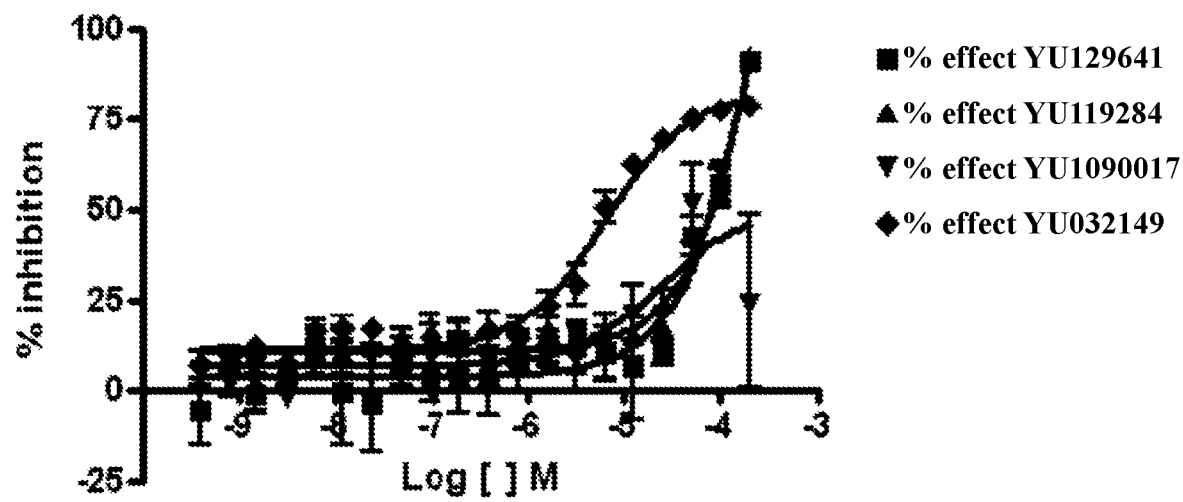
FIG. 2A comprises a graph depicting dose response of MKP-5 activity for exemplary compounds of the invention.
Figure 2B:
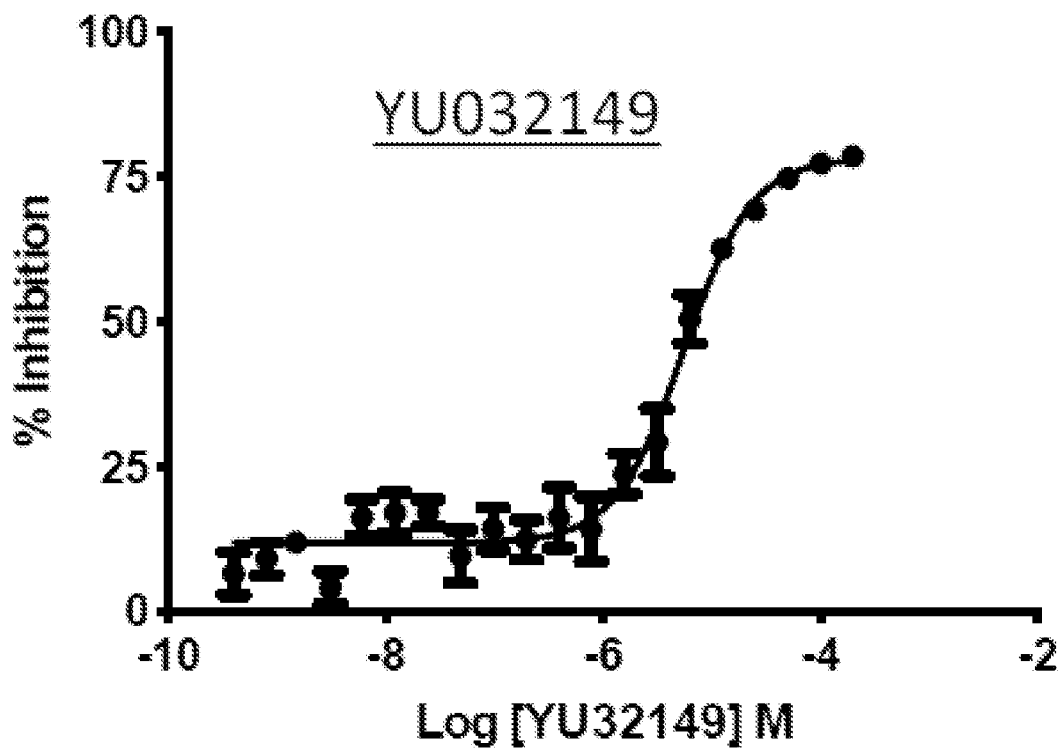
FIG. 2B comprises a graph illustrating the dose response of MKP-5 for an exemplary compound of the invention (YU032149).
Figure 2C:
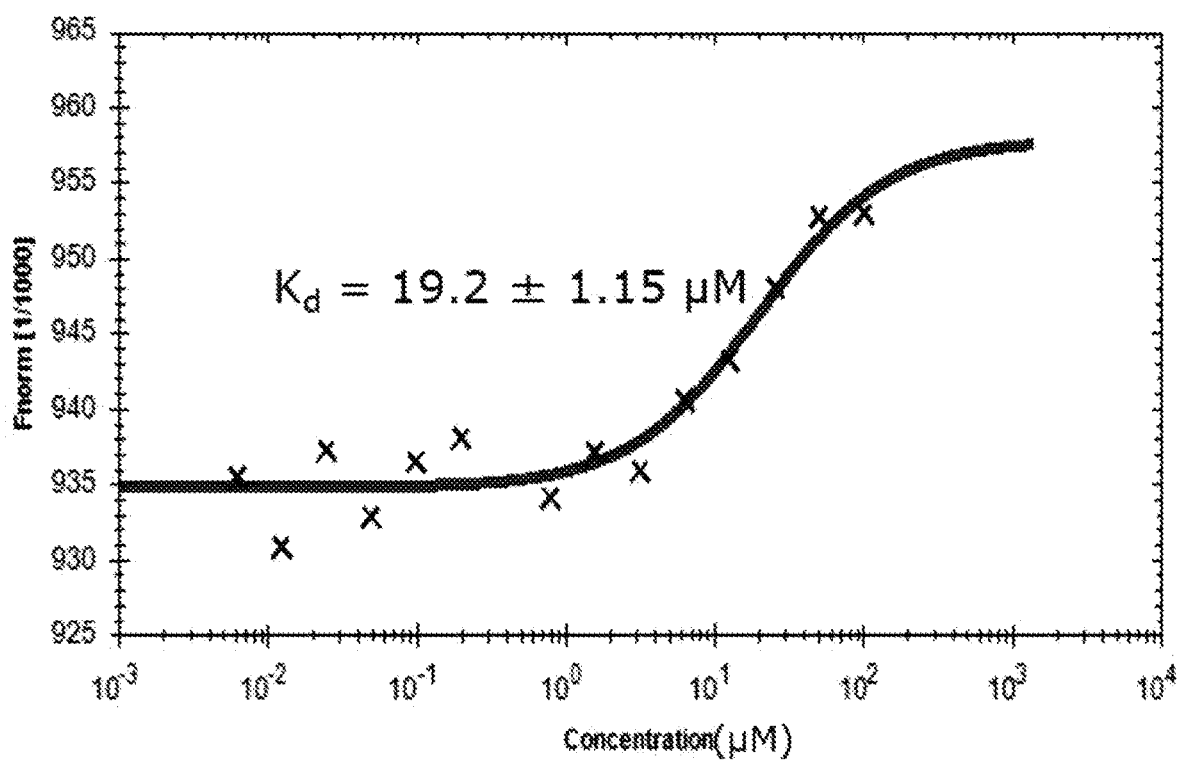
FIG. 2C comprises a graph depicting determination of $K_d$ of YU032149 with MKP-5.

Compounds from the pilot collection consisting of Microsource GenPlus, Microsource Natural Product, NIH Clinical collections, ChemBridge DIVERSet, ChemBridge MicroFormats, Maybridge Diversity, and ChemBridge Amines and Alcohols were screened. Assay conditions were 1.5 µM MKP-5 and 25 µM dual phosphorylated peptide DDE (Nle)(pT)G(pY)VATR (10 µL total volume), incubated for 30 minutes at 37° C. followed by addition of 40 µL Malachite Green reagent. Z' values are ~0.7-0.8. Malachite green reagent was made by combining 30 mL 0.045% Malachite Green (Sigma #M-9636) with 20 mL 4.2% ammonium molybdate in 4 M HCl, shaking for at least 30 mins and adding 0.01% Tween 20. The dose response for the four most potent compounds (structures below) is shown in FIG. 2 and Table 1.

The following % inhibition data form MKP-5 were obtained at 12.5 µM of compound concentration: YU252252, 37%; YU241658, 15%; YU241659, 12%.

TABLE 1

| | Kd (M) | MKP5 EZReader fluor _TpY | MKP5 EZREader fluor pT_Y | MKP5 Malachite pTpY | STEP40 Malachite pTpY | MKP5 pNPP pTpY | STEP40 pNPP pTpY |
|---|---|---|---|---|---|---|---|
| YU129641 | 1.04E−05 | 1.41E−05 | >.0001 | >.0001 | >.0002 | >.0002 |
| YU119284 | >.0002 | >.0002 | >.0001 | >.0001 | >.0002 | >.0002 |

TABLE 1-continued

| Kd (M) | MKP5 EZReader fluor_TpY | MKP5 EZREader fluor pT_Y | MKP5 Malachite pTpY | STEP40 Malachite pTpY | MKP5 pNPP pTpY | STEP40 pNPP pTpY |
|---|---|---|---|---|---|---|
| YU109017 | 1.03E−05 | 1.56E−05 | >.0001 | >.0001 | >.0001 | >.0002 |
| YU032149 | 1.75E−05 | 1.13E−05 | 6.25E−06 | >.0002 | 4.26E−06 | >.0002 | fluor_TpY FITC-Aha-Asp-Glu-Leu-Thr-Gly-pTyr-Val-Ala-Thr-Arg-(CONH2)

fluor pT_Y FITC-Aha-Asp-Glu-Leu-pThr-Gly-Tyr-Val-Ala-Thr-Arg-(CONH2)

pTpY Asp-Asp-Glu-Nle-pThr-Gly-pTyr-Val-Ala-Thr-Arg-(COOH)

fluor_TpY SEQ ID NO:1 fluor pT_Y SEQ ID NO:2 pTpY SEQ ID NO:3

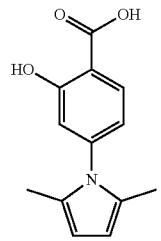

YU129641

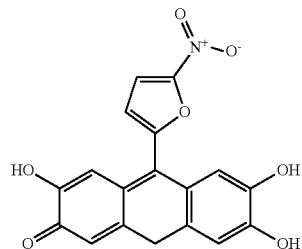

YU109017

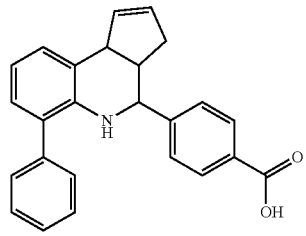

YU119284

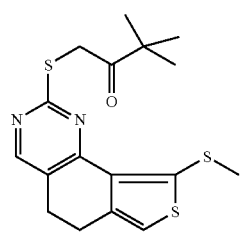

YU032149

Example 2: Crystal Structure of Human MKP-5

Figure 3:
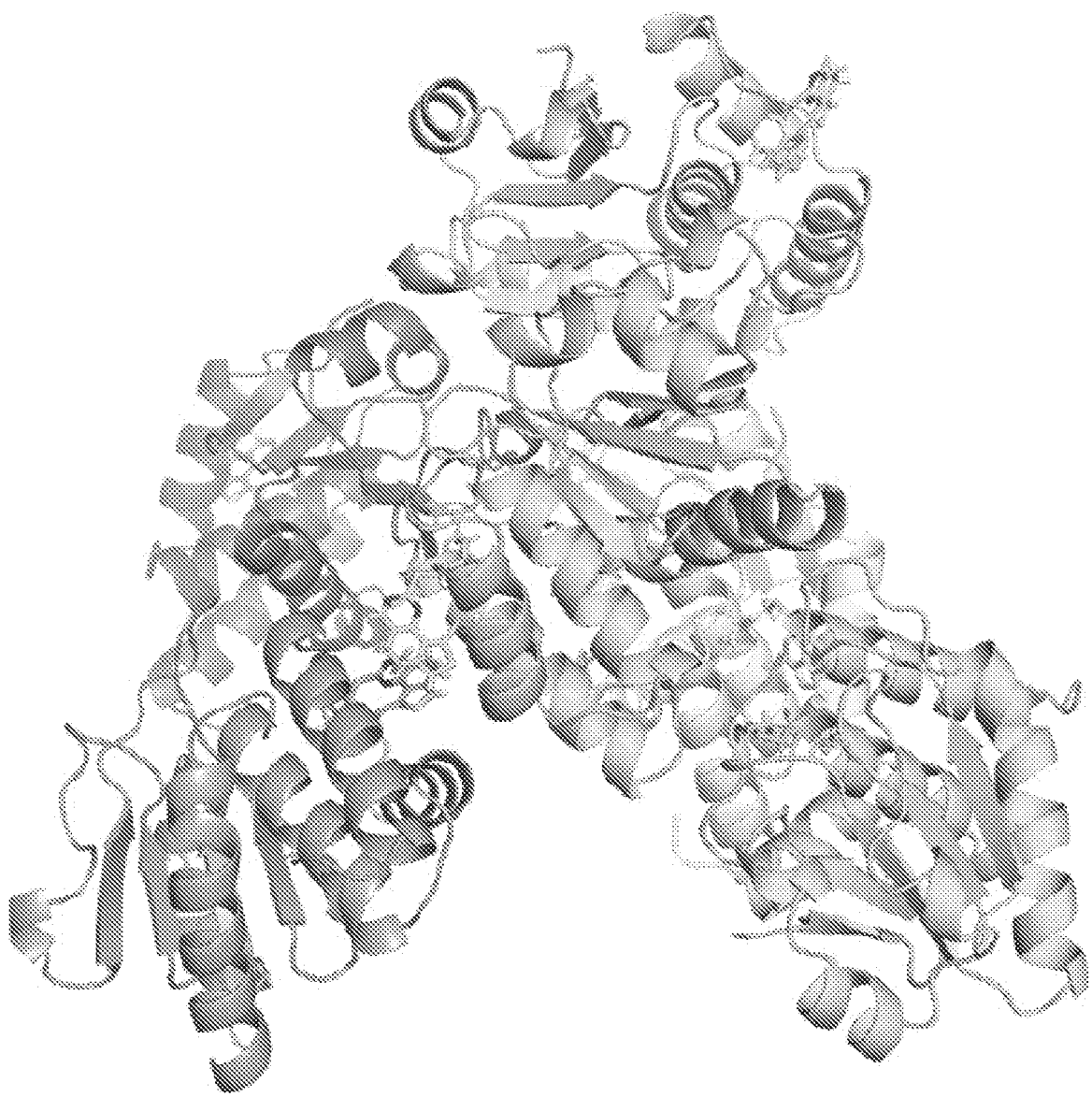
FIG. 3 comprises a ribbon diagram based on the crystal structure of MKP-5 with ligand and inhibitor bound.

Crystallization was achieved using the hanging drop vapor diffusion method with 12 mg/mL protein concentration and 5 mM inhibitor (YU032149, formula 3), incubated at 4° C. Well solution contained 200 mM ammonium acetate, 100 mM HEPES (pH 7.5), 25% w/v PEG 3350. Crystals grew in 4-7 days. Mother liquor with an additional 3% w/v PEG 3350 was used as cryoprotectant. A ribbon diagram of the structure is shown in FIG. 3. Data statistics are shown in Table 2.

TABLE 2

|  | MKP5CD: YU032149 |
| --- | --- |
| Data Collection |  |
| Space Group | P 1 21 1 |
| Cell Dimensions |  |
| a, b, c (Å) | 66.5, 129.4, 83.5 |
| α, β, γ (°) | 90, 91.7, 90 |
| Resolution (Å) | 40.89-3.09 |
| $R_{meas}$ | 0.244 (0.961) |
| I/σI | 7.5 (1.8) |
| Completeness (%) | 98.2 (100) |
| Redundancy | 3.8 (4.2) |
| Refinement |  |
| Resolution (Å) | 41.73-3.20 |
|  | (3.33-3.20) |
| No. reflections | 25,718 |
| (unique) | (2,503) |
| $R/R_{free}$ | 20.6/25.7 |
|  | (25.4/27.8) |
| RMS deviations |  |
| Bond lengths (Å) | .003 |
| Bond angles (°) | .517 |
| Ramachandran | 94/5.7/0.2 |
| Favored/Allowed/ |  |
| Outlier (%) |  |
| Clashscore | 2.51 |
| Average B-factor | 34.00 |
| Protein | 33.99 |
| Ligand | 34.43 |

Figure 4A:
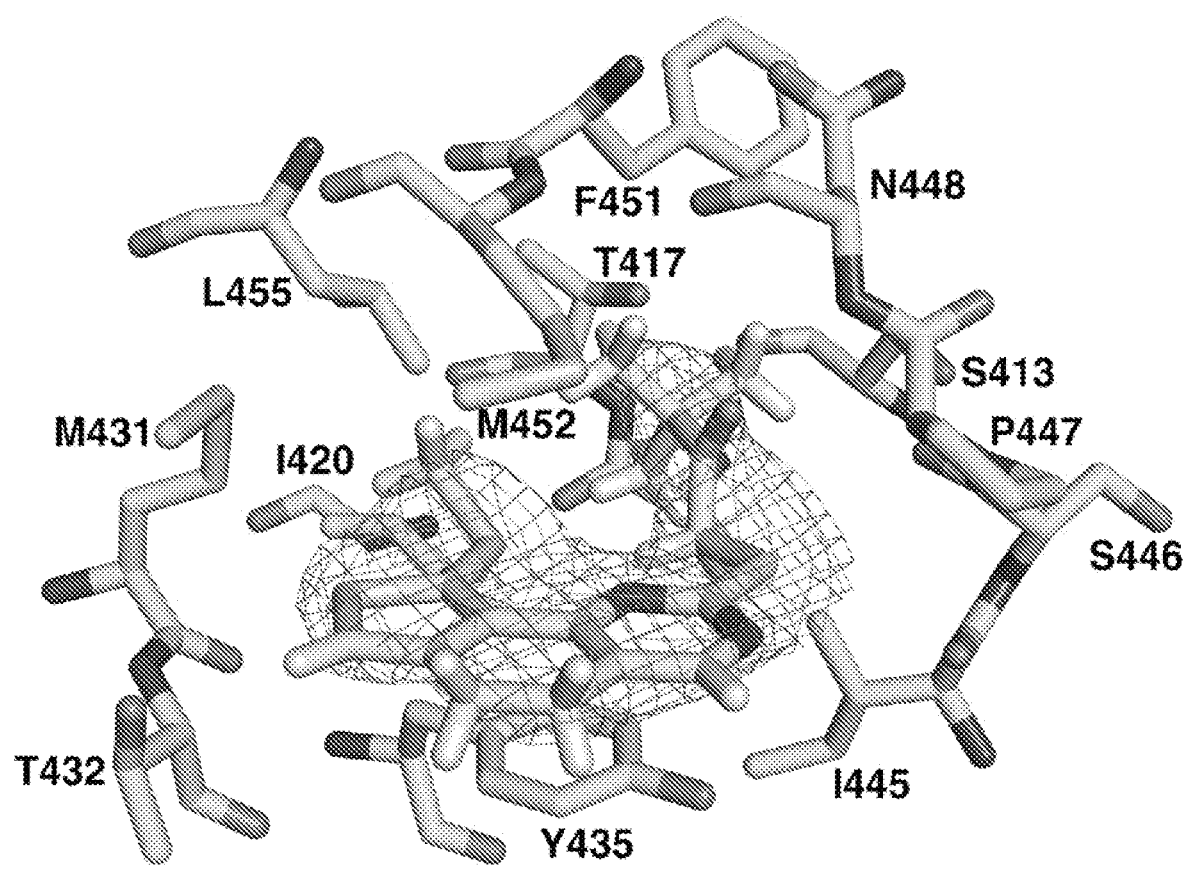
FIG. 4A comprises an illustration of binding of YU032149 to MKP-5, with certain residues illustrated.
Figure 4B:
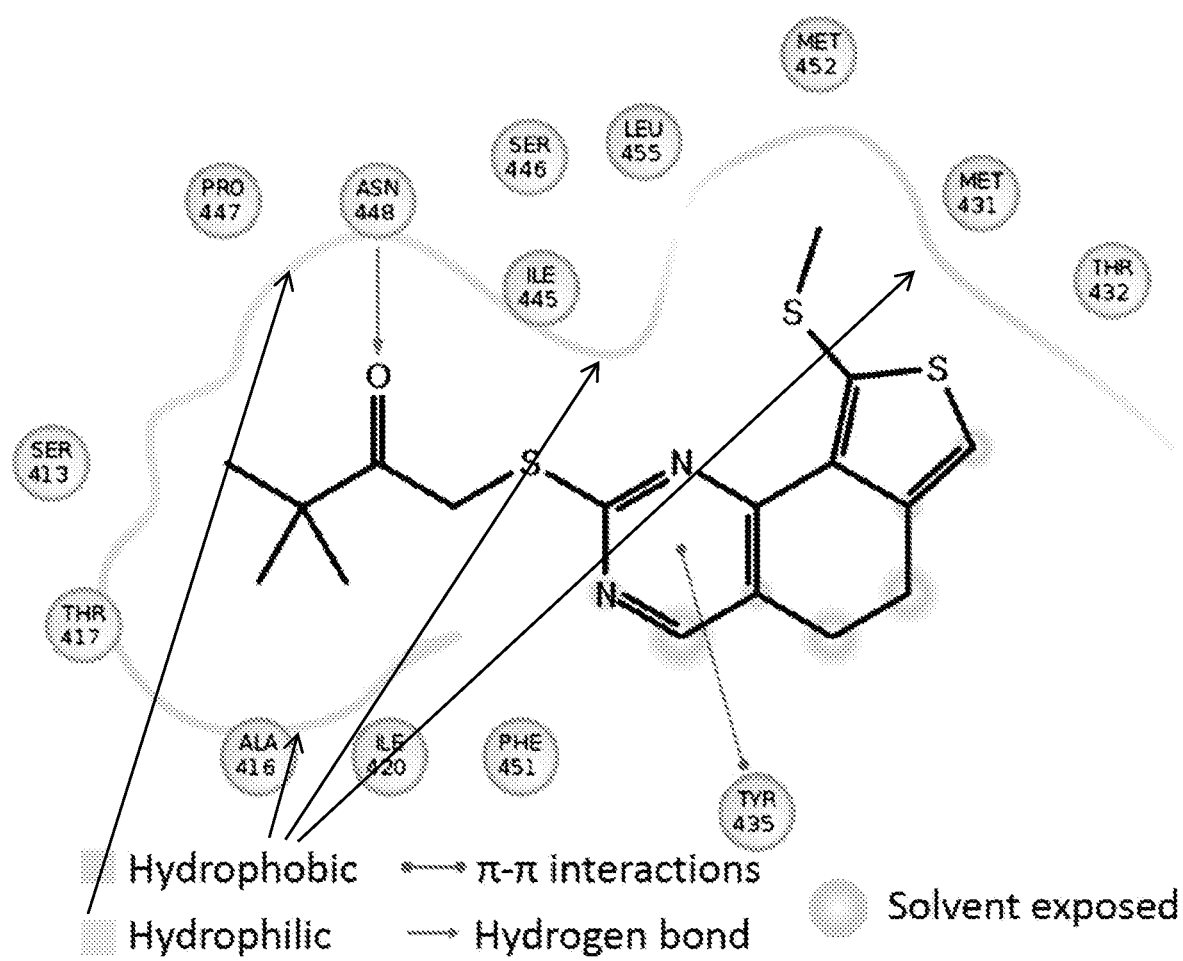
FIG. 4B comprises an illustration of YU032149 to the allosteric site, with certain contacts between inhibitor and protein illustrated.
Figure 5:
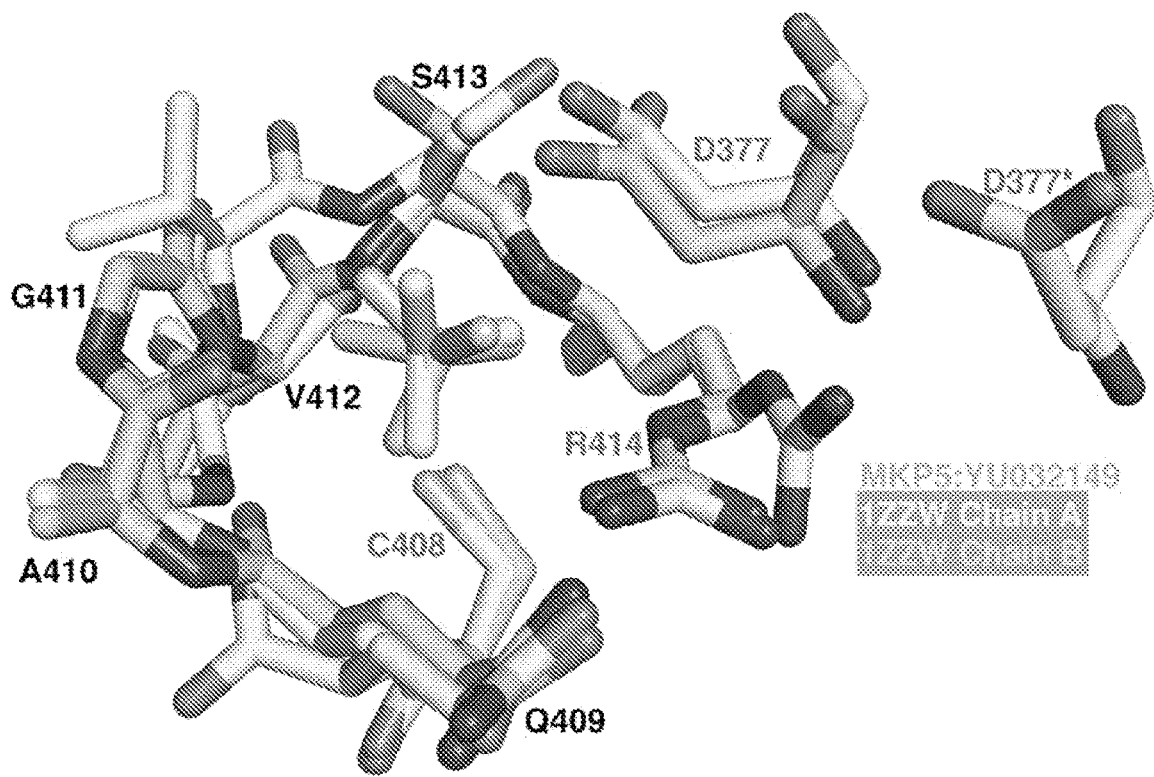
FIG. 5 comprises an illustration of binding of YU032149 to the allosteric site of MKP-5. Displacement of selected active site residues in response to the binding is illustrated.

Without wishing to be limited by theory, YU032149 appears based on the crystal structure to inhibit MKP-5 by binding to an allosteric site which initiates a conformational change in the protein that ultimately decreases the volume of the catalytic site by 30%. Contacts between residues in the allosteric site and YU032149 are shown in FIG. 4. Displacement of active site residues is shown in FIG. 5.

Example 3: Other Inhibitors of MKP-5

Figure 6:
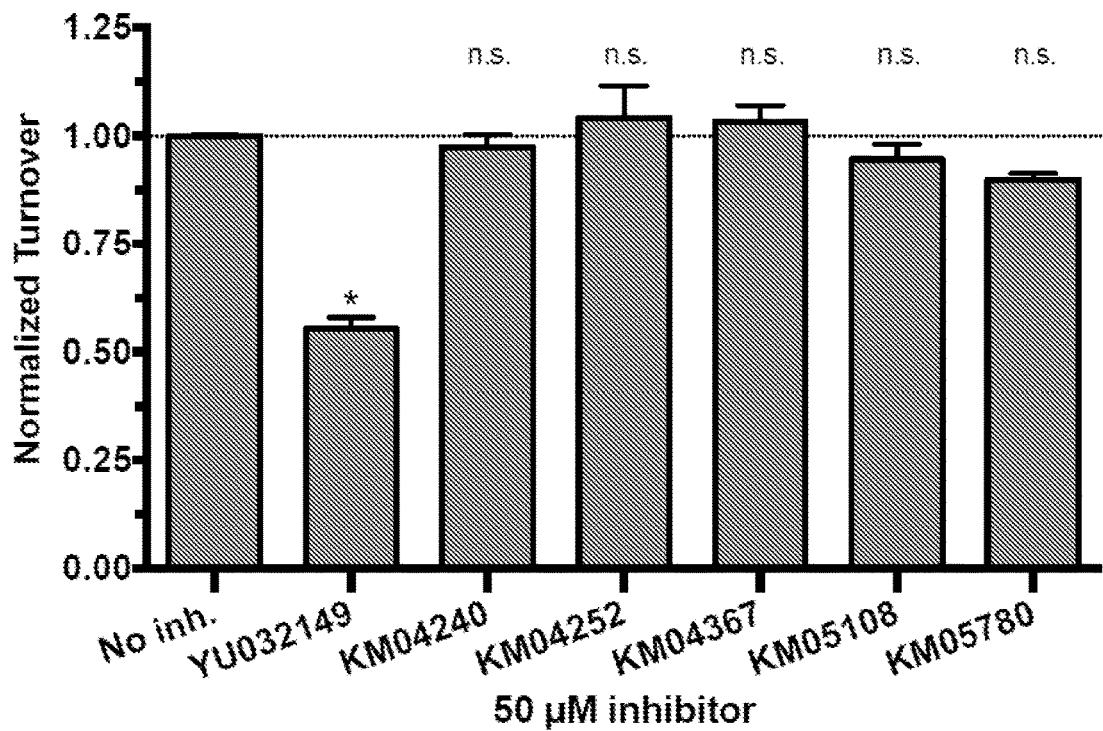
FIG. 6 comprises a bar graph illustrating normalized turnover for selected analogs of YU032149 (50 µM inhibitor in each test).
Figure 7A:
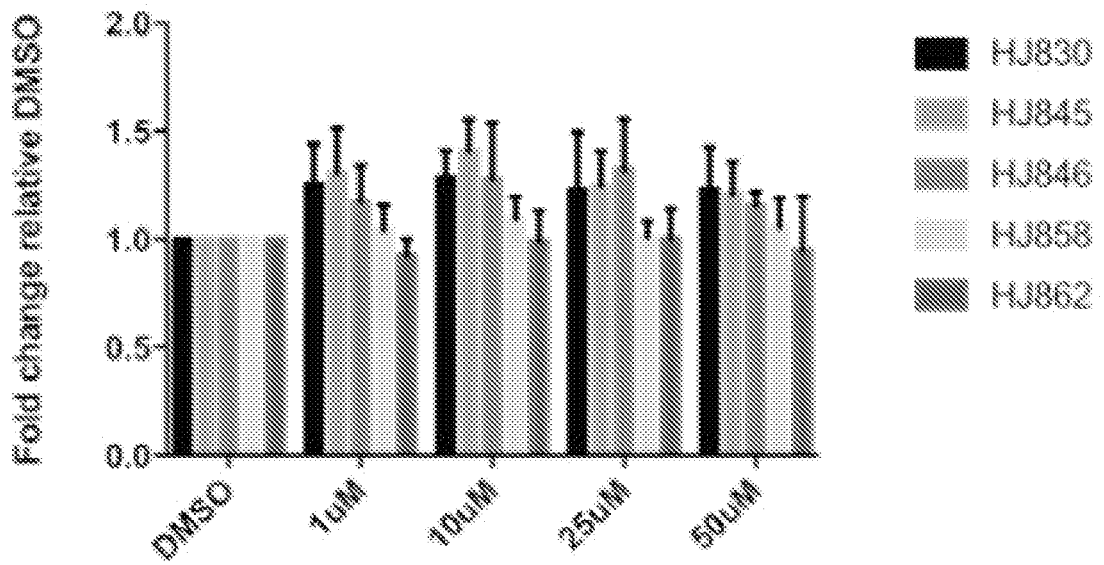
FIGS. 7A-7C comprise a series of bar graphs illustrating MAPK activity assays for selected compounds.
Figure 7B:
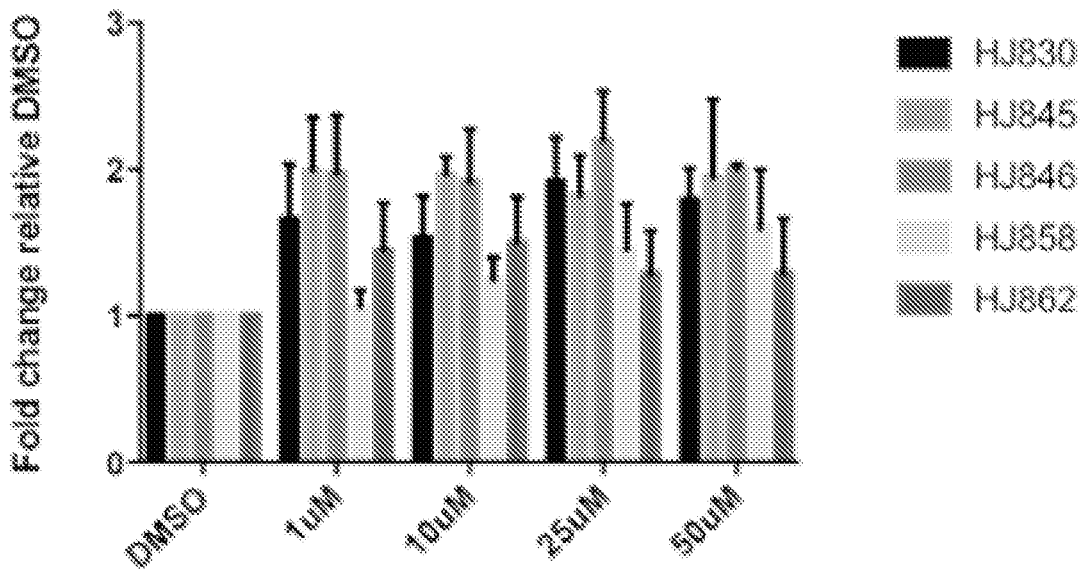
Figure 7C:
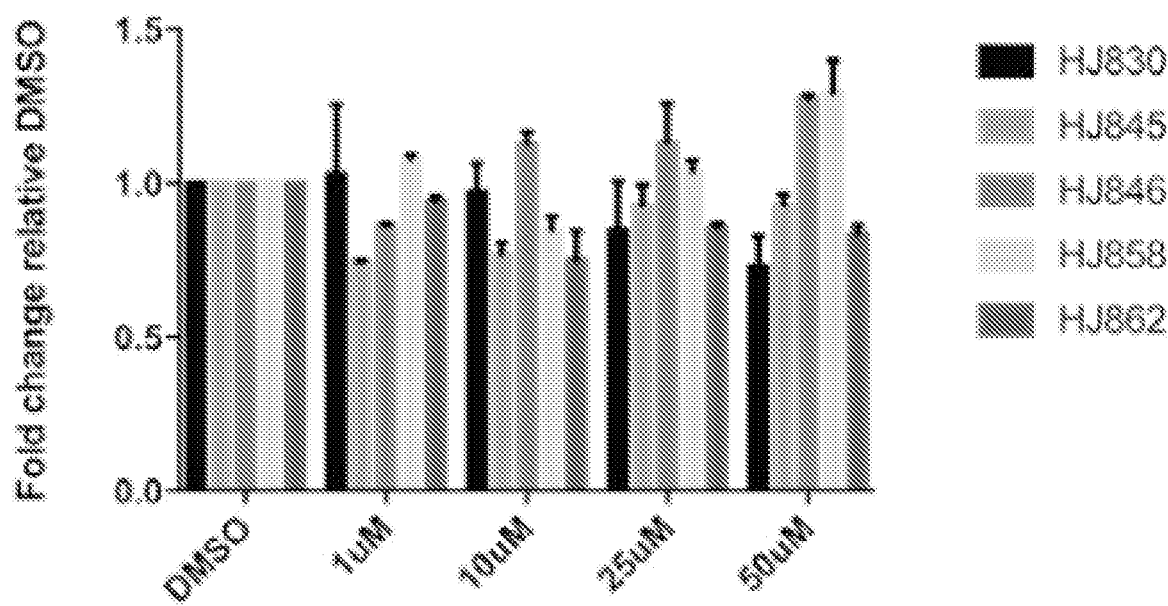

Commercially available derivatives of YU032149 were evaluated for activity against MKP-5. The results are shown in FIG. 6. A series of compounds, herein referred to as the HJ series, was derived from the YU032149 core based on the co-crystal structure. Structures are shown above. Activity data for the HJ series is shown in FIG. 7.

Example 4: Synthesis of the HJ Series

An illustrative scheme applicable to certain compounds contemplated within the invention is provided herein:

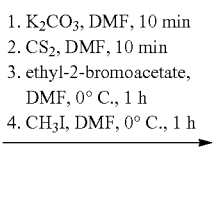

1. $K_2CO_3$, DMF, 10 min
2. $CS_2$, DMF, 10 min
3. ethyl-2-bromoacetate, DMF, 0° C., 1 h
4. $CH_3I$, DMF, 0° C., 1 h

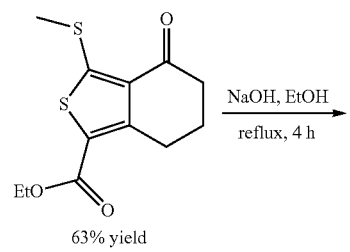

63% yield

NaOH, EtOH
reflux, 4 h

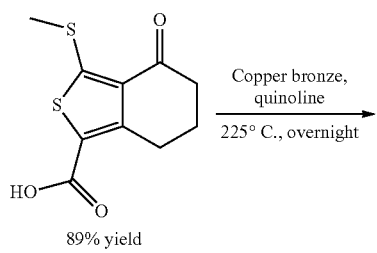

89% yield

Copper bronze, quinoline
225° C., overnight

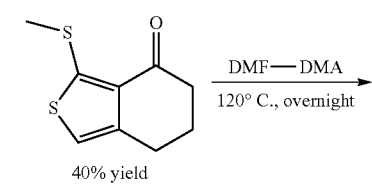

40% yield

DMF—DMA
120° C., overnight

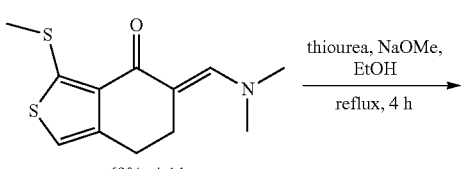

69% yield

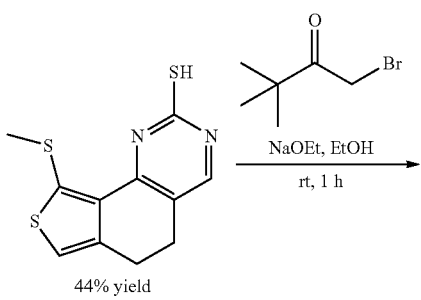

44% yield

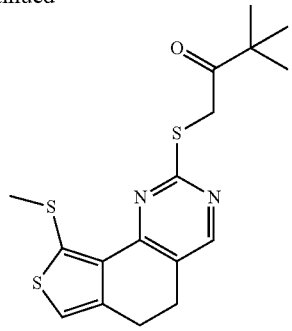

YUO32149
HJ844
73% yield

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of inhibiting mitogen-activated protein (MAP) kinase phosphatase-5 (MKP-5) in a mammal, the method comprising administering to the mammal a therapeutically effective amount of a compound of formula (1a) or (1b):

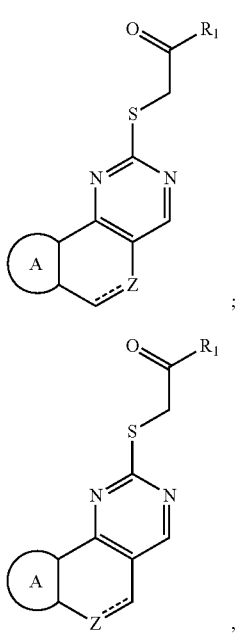

wherein:
- Z is selected from the group consisting of NR, NC(=O)R, CH$_2$, and O and the ═══ bond is single; or
- Z is N and the ═══ bond is double;
- R$_1$ is selected from the group consisting of C$_1$-C$_6$ alkyl, optionally substituted phenyl, and NRR;
- each occurrence of R is independently selected from the group consisting of H, C$_1$-C$_6$ alkyl, and optionally substituted phenyl;
- A is optionally substituted phenyl or optionally substituted thiophenyl.

2. The method of claim 1, wherein the compound is the compound of formula (2):

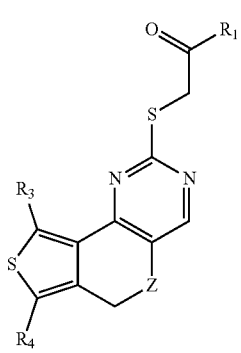

wherein:
- Z is selected from the group consisting of CH$_2$ and O;
- R$_1$ is selected from the group consisting of C$_1$-C$_6$ alkyl, optionally substituted phenyl, and NRR,
  - where each occurrence of R is independently selected from the group consisting of H, C$_1$-C$_3$ alkyl, and substituted or unsubstituted phenyl;
- R$_3$ is selected from the group consisting of H, C$_1$-C$_6$ alkyl, and C$_1$-C$_3$ thioether; and
- R$_4$ is selected from the group consisting of H and COOR$_5$, where R$_5$ is selected from the group consisting of H and C$_1$-C$_6$ alkyl.

3. The method of claim 1, wherein the phenyl or thiophenyl of A is substituted with at least one substituent selected from the group consisting of C$_1$-C$_6$ alkyl, C$_1$-C$_6$ thioalkyl, C(=O)OH, C(=O)OC$_1$-C$_6$ alkyl, cyano, and halogen.

4. The method of claim 1, wherein the compound has a Ki≤100 μM against MKP-5.

5. The method of claim 1, wherein the compound binds to an allosteric site of MKP-5.

6. A compound selected from the group consisting of
- 1-((5,6-dihydrobenzo[h]quinazolin-2-yl)thio)-3,3-dimethylbutan-2-one;
- N,N-dimethyl-2-((9-(methylthio)-5,6-dihydrothieno[3,4-h]quinazolin-2-yl)thio)acetamide;
- N-ethyl-N-methyl-2-((9-(methylthio)-5,6-dihydrothieno[3,4-h]quinazolin-2-yl)thio)acetamide;
- 1-((9-fluoro-5,6-dihydrobenzo[h]quinazolin-2-yl)thio)-3,3-dimethylbutan-2-one;
- 1-((6H-isochromeno[4,3-d]pyrimidin-2-yl)thio)-3,3-dimethylbutan-2-one;
- 1-((5,6-dihydrothieno[2,3-h]quinazolin-2-yl)thio)-3,3-dimethylbutan-2-one;
- 3,3-dimethyl-1-(pyrimido[5,4-c]quinolin-2-ylthio)butan-2-one;
- 1-((6-acetyl-5,6-dihydropyrimido[5,4-c]quinolin-2-yl)thio)-3,3-dimethylbutan-2-one; and
- 3,3-dimethyl-1-((9-propyl-5,6-dihydrothieno[3,4-h]quinazolin-2-yl)thio)butan-2-one.

7. A compound selected from the group consisting of:

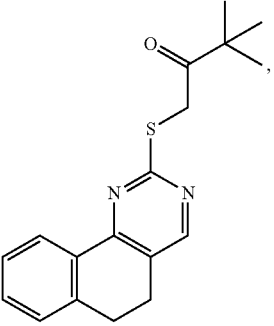

HJ830

-continued

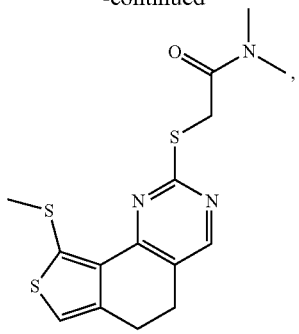

HJ845

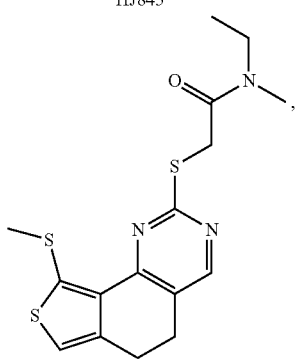

HJ846

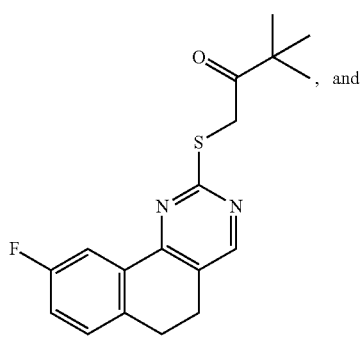, and

HJ858

-continued

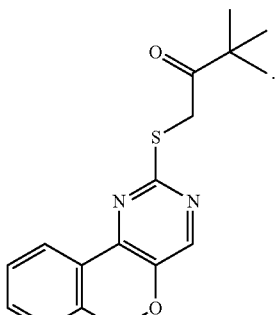

HJ862

8. The method of claim 1, wherein the compound is administered as part of a pharmaceutical composition further comprising at least one pharmaceutically acceptable carrier.

9. The method of claim 1, wherein the mammal is a human.

10. The method of claim 1, wherein the compound is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

11. The method of claim 1, further comprising administering to the mammal at least one additional agent that inhibits MKP-5 in the mammal.

12. The method of claim 11, wherein the compound and at least one additional agent are coformulated.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MOD
<222> LOCATION: (1)..(1)
<223> OTHER INFORMATION: N-terminus derivatived with FITC-AHA
      [5-(fluorescein-amido)hexylacrylic acid]
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (10)..(10)
<223> OTHER INFORMATION: AMIDATION

<400> SEQUENCE: 1

Asp Glu Leu Thr Gly Tyr Val Ala Thr Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (1)..(1)
<223> OTHER INFORMATION: N-terminus derivatived with FITC-AHA
      [5-(fluorescein-amido)hexylacrylic acid]
<220> FEATURE:
<221> NAME/KEY: MOD_RES
<222> LOCATION: (4)..(4)
<223> OTHER INFORMATION: PHOSPHORYLATION
<220> FEATURE:
```

```
<221> NAME/KEY: MOD_RES
<222> LOCATION: (10)..(10)
<223> OTHER INFORMATION: AMIDATION

<400> SEQUENCE: 2

Asp Glu Leu Thr Gly Tyr Val Ala Thr Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 3

Asp Asp Glu Xaa Tyr Gly Tyr Val Ala Thr Arg
1               5                   10

<210> SEQ ID NO 4
<211> LENGTH: 482
<212> TYPE: PRT
<213> ORGANISM: Homo sapiens

<400> SEQUENCE: 4

Met Pro Pro Ser Pro Leu Asp Asp Arg Val Val Ala Leu Ser Arg
1               5                   10                  15

Pro Val Arg Pro Gln Asp Leu Asn Leu Cys Leu Asp Ser Ser Tyr Leu
            20                  25                  30

Gly Ser Ala Asn Pro Gly Ser Asn Ser His Pro Pro Val Ile Ala Thr
        35                  40                  45

Thr Val Val Ser Leu Lys Ala Ala Asn Leu Thr Tyr Met Pro Ser Ser
    50                  55                  60

Ser Gly Ser Ala Arg Ser Leu Asn Cys Gly Cys Ser Ser Ala Ser Cys
65                  70                  75                  80

Cys Thr Val Ala Thr Tyr Asp Lys Asp Asn Gln Ala Gln Thr Gln Ala
                85                  90                  95

Ile Ala Ala Gly Thr Thr Thr Thr Ala Ile Gly Thr Ser Thr Thr Cys
            100                 105                 110

Pro Ala Asn Gln Met Val Asn Asn Asn Glu Asn Thr Gly Ser Leu Ser
        115                 120                 125

Pro Ser Ser Gly Val Gly Ser Pro Val Ser Gly Thr Pro Lys Gln Leu
    130                 135                 140

Ala Ser Ile Lys Ile Ile Tyr Pro Asn Asp Leu Ala Lys Lys Met Thr
145                 150                 155                 160

Lys Cys Ser Lys Ser His Leu Pro Ser Gln Gly Pro Val Ile Ile Asp
                165                 170                 175

Cys Arg Pro Phe Met Glu Tyr Asn Lys Ser His Ile Gln Gly Ala Val
            180                 185                 190

His Ile Asn Cys Ala Asp Lys Ile Ser Arg Arg Arg Leu Gln Gln Gly
```

```
            195                 200                 205

Lys Ile Thr Val Leu Asp Leu Ile Ser Cys Arg Glu Gly Lys Asp Ser
    210                 215                 220

Phe Lys Arg Ile Phe Ser Lys Glu Ile Ile Val Tyr Asp Glu Asn Thr
225                 230                 235                 240

Asn Glu Pro Ser Arg Val Met Pro Ser Gln Pro Leu His Ile Val Leu
                245                 250                 255

Glu Ser Leu Lys Arg Glu Gly Lys Glu Pro Leu Val Leu Lys Gly Gly
            260                 265                 270

Leu Ser Ser Phe Lys Gln Asn His Glu Asn Leu Cys Asp Asn Ser Leu
            275                 280                 285

Gln Leu Gln Glu Cys Arg Glu Val Gly Gly Gly Ala Ser Ala Ala Ser
            290                 295                 300

Ser Leu Leu Pro Gln Pro Ile Pro Thr Thr Pro Asp Ile Glu Asn Ala
305                 310                 315                 320

Glu Leu Thr Pro Ile Leu Pro Phe Leu Phe Leu Gly Asn Glu Gln Asp
                325                 330                 335

Ala Gln Asp Leu Asp Thr Met Gln Arg Leu Asn Ile Gly Tyr Val Ile
            340                 345                 350

Asn Val Thr Thr His Leu Pro Leu Tyr His Tyr Glu Lys Gly Leu Phe
            355                 360                 365

Asn Tyr Lys Arg Leu Pro Ala Thr Asp Ser Asn Lys Gln Asn Leu Arg
            370                 375                 380

Gln Tyr Phe Glu Glu Ala Phe Glu Phe Ile Glu Glu Ala His Gln Cys
385                 390                 395                 400

Gly Lys Gly Leu Leu Ile His Cys Gln Ala Gly Val Ser Arg Ser Ala
                405                 410                 415

Thr Ile Val Ile Ala Tyr Leu Met Lys His Thr Arg Met Thr Met Thr
            420                 425                 430

Asp Ala Tyr Lys Phe Val Lys Gly Lys Arg Pro Ile Ile Ser Pro Asn
            435                 440                 445

Leu Asn Phe Met Gly Gln Leu Leu Glu Phe Glu Glu Asp Leu Asn Asn
            450                 455                 460

Gly Val Thr Pro Arg Ile Leu Thr Pro Lys Leu Met Gly Val Glu Thr
465                 470                 475                 480

Val Val
```